United States Patent [19]

Charlton et al.

[11] Patent Number: 4,645,744

[45] Date of Patent: Feb. 24, 1987

[54] UNIFIED TEST MEANS FOR ION DETERMINATION

[75] Inventors: Steven C. Charlton, Elkhart, Ind.; Roger L. Fleming, Niles, Mich.; Paul Hemmes, Elkhart; Arthur L. Y. Lau, Mishawaka, both of Ind.

[73] Assignee: Miles Laboratories, Inc., Elkhart, Ind.

[21] Appl. No.: 751,185

[22] Filed: Jul. 2, 1985

Related U.S. Application Data

[63] Continuation-in-part of Ser. No. 493,983, May 12, 1983, abandoned.

[51] Int. Cl.$^4$ .................... G01N 21/78; G01N 33/52
[52] U.S. Cl. ........................ 436/74; 422/56; 436/79; 436/175
[58] Field of Search ............. 422/56, 57, 58; 436/73, 436/74, 79, 172, 175

[56] References Cited

U.S. PATENT DOCUMENTS

| | | | |
|---|---|---|---|
| 3,368,872 | 2/1968 | Natelson | 422/56 X |
| 3,562,129 | 2/1971 | Simon | 204/195 M |
| 3,630,957 | 12/1971 | Rey et al. | 422/56 X |
| 3,635,679 | 1/1972 | Bloch et al. | 436/169 X |
| 3,992,158 | 11/1976 | Przybylowicz et al. | 422/58 X |
| 4,003,707 | 1/1977 | Lubbers et al. | |
| 4,061,468 | 12/1977 | Lange et al. | 422/56 |
| 4,225,410 | 9/1980 | Pace | 422/98 X |
| 4,231,754 | 11/1980 | Vogelhut | 422/56 X |
| 4,260,392 | 4/1981 | Lee | 422/56 X |
| 4,272,484 | 6/1981 | Lubbers | 422/68 |
| 4,272,485 | 6/1981 | Lubbers | 422/68 |
| 4,367,072 | 1/1983 | Vogtle et al. | 436/501 |
| 4,540,520 | 9/1985 | Charlton et al. | 260/396 N |
| 4,552,697 | 11/1985 | Yip et al. | 260/396 N |

FOREIGN PATENT DOCUMENTS 0041175 12/1981 European Pat. Off. .
2842862 4/1980 Fed. Rep. of Germany ........ 436/74

OTHER PUBLICATIONS

Feinstein et al., Proc. Nat. Acad. Sci., USA, vol. 68, No. 9, pp. 2037–2041, Sep. 1971.
Kusnir et al., Chemical Abstracts, vol. 82, 1975, No. 51257q.
Sumiyoshi et al., Chemical Abstracts, vol. 89, 1978, No. 89:55833s.

*Primary Examiner*—Arnold Turk
*Attorney, Agent, or Firm*—Mary G. Boguslaksi

[57] ABSTRACT

A test means, test device and method for use for determining the presence of an ion in a test sample are disclosed. The test means comprises a substantially nonpolar, nonporous carrier matrix incorporated with an ionophore capable of forming a complex with the specific ion and reporter substance capable of interacting with the complex of ionophore and ion to produce a detectable response. The test means disclosed is particularly useful for serum potassium determinations. The test means forms the reagent layer in a multilayer format particularly suited to whole blood electrolyte determinations.

34 Claims, 7 Drawing Figures

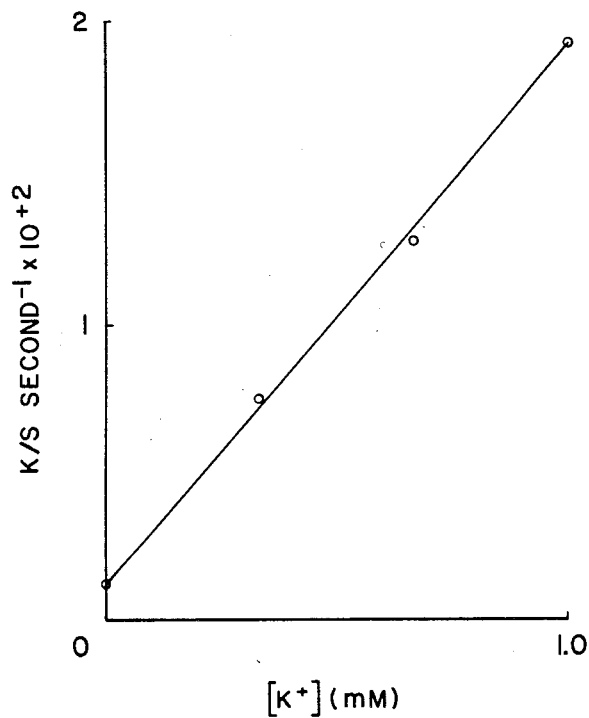
FIG. I
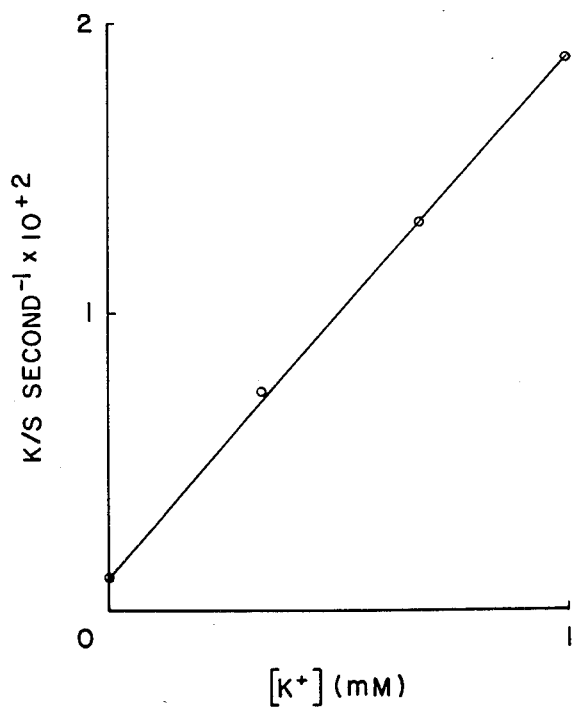
FIG. II

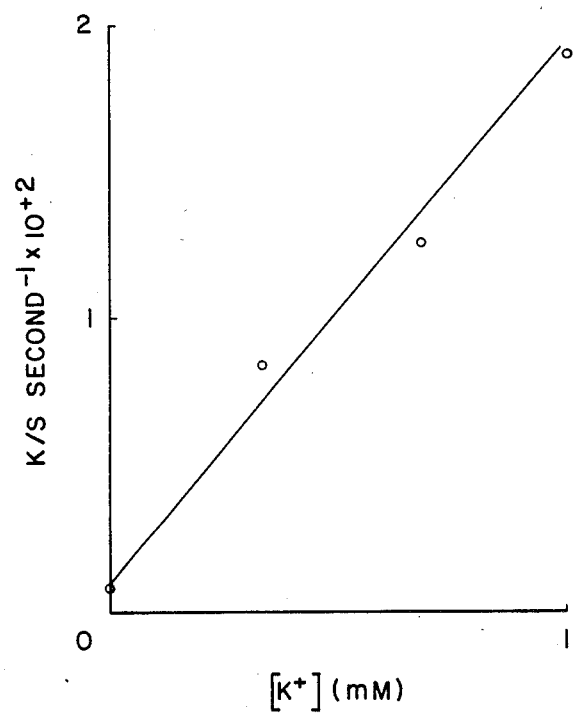
FIG. III
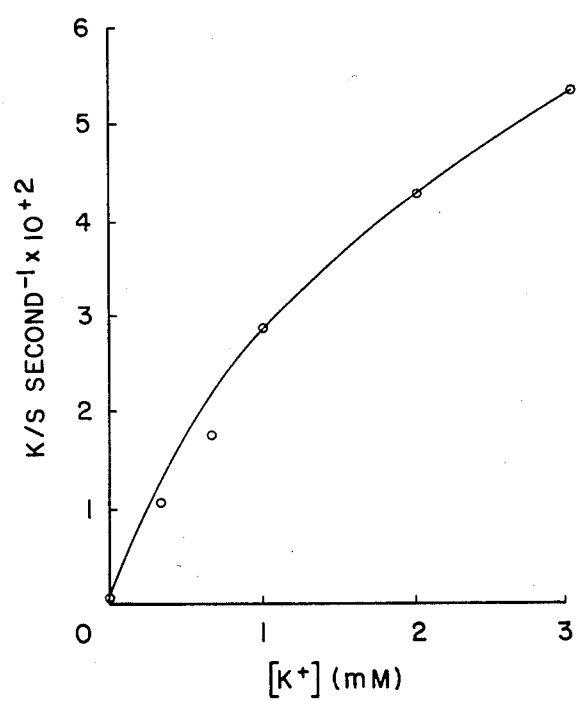
FIG. IV

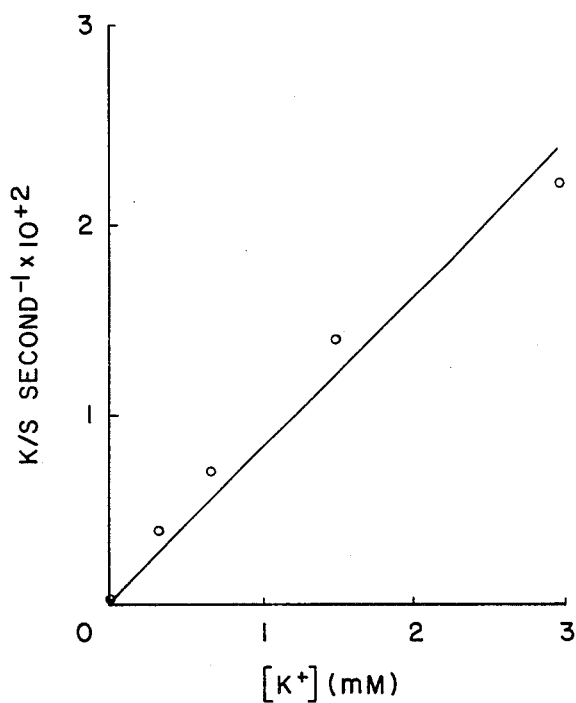
FIG. V
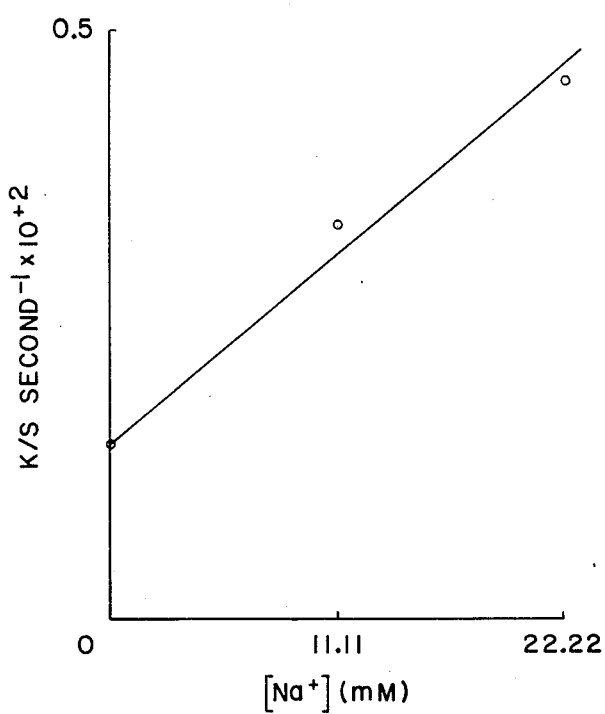
FIG. VI

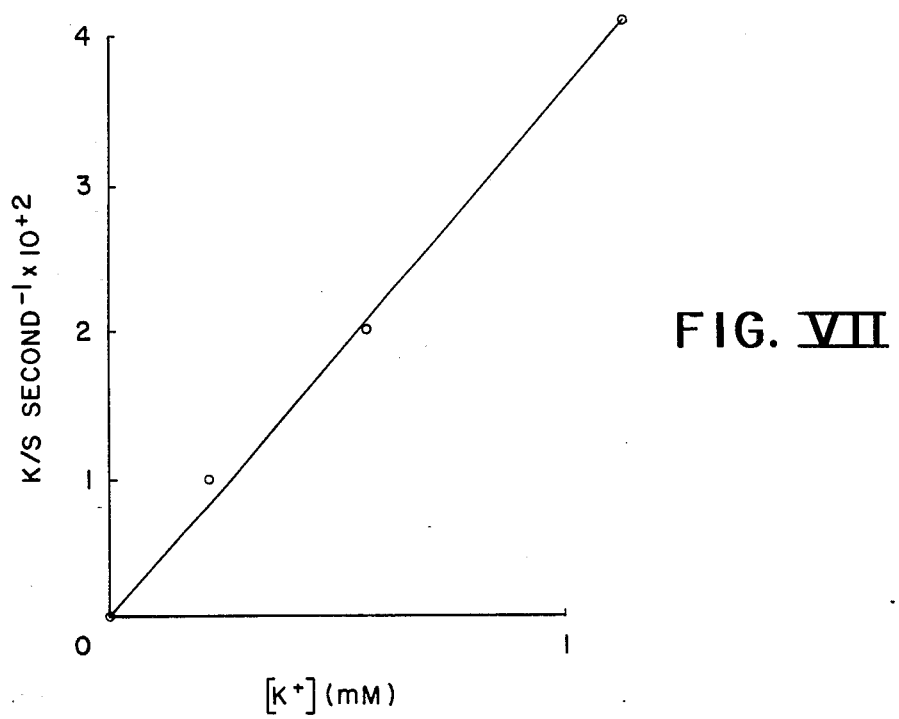
FIG. VII

UNIFIED TEST MEANS FOR ION DETERMINATION

CROSS REFERENCE TO RELATED APPLICATION

This application is a continuation-in-part of U.S. Ser. No. 493,983, filed May 12, 1983, now abandoned.

1. INTRODUCTION

The present invention relates to the measurement of ions, in particular ions in aqueous solution, and to a test means or device for performing such measurements. The invention provides a convenient format for determining the presence and/or concentration of such ions whereby results are available shortly after contacting an aqueous test sample with the test means or device. Cumbersome, expensive electronic equipment such as ion-specific electrodes, flame photometers, atomic absorption spectrophotometers or the like is not needed. The present invention enables the user merely to contact the test sample with the test device or similar test means configuration according to the present invention, and determine any detectable response.

The determination of aqueous ion concentration has application in numerous technologies. In the water purification art, calcium concentration must be carefully monitored to assess the degree of saturation of an ion exchange resin deionizer. Measurement of sodium and other ions in seawater is important in the preparation of drinking water aboard a ship at sea. Measurement of the potassium level in blood aids the physician in diagnosis of conditions leading to muscle irritability and excitatory changes in myocardial function and conditions such as oliguria, anuria, urinary obstruction and renal failure due to shock. The measurement of potassium in serum is particularly important clinically. Since the clinical range of serum potassium is only from about 2 to about 10 millimolar with a normal range from about 3.5 to 5.5 mM, the measurement requires high sensitivity and precision. Measurement of lithium levels in the blood are also important since the toxic dose levels are only slightly higher than the therapeutic levels used in psychiatric treatment.

Needless to say, a sensitive, convenient and inexpensive method for determining ion concentration would greatly enhance the state of these technologies, as well as any others where such rapid, accurate determinations would be beneficial. Thus, for example, if a medical laboratory technician could accurately measure the potassium or calcium ion level of a serum or whole blood sample in a matter of seconds or minutes, such rapid results would increase laboratory efficiency and aid the physician in diagnosis.

2. INFORMATION DISCLOSURE

Methods for determining ions in solution included flame photometry, atomic absorption photometry and ion-specific electrodes. Test strip formats have been disclosed in copending U.S. patent application Nos. 493,969, 493,983, 493,982 and 583,127 assigned commonly herein. The use of certain compounds and compositions which selectively isolate ions from the sample solution has become popular in ion-specific electrodes. These compounds, known as ionophores, have the capability of transporting ions into an electrode membrane thereby causing a difference in potential which can be measured. Ion assays utilizing the ion/ionophore phenomenon include membrane electrodes, liquid/liquid partitioning, fluorescence and test strips.

2.1 Ion-Specific Electrodes

When two solutions having different concentrations of ions are separated by an electrically conductive membrane, an electrical potential (EMF) is generated. In membrane separation cells, the membrane can be a simple fritted glass barrier, allowing a small but measurable degree of ion diffusion from one solution to the other. Alternatively, a nonporous, electrically nonconductive film, such as polyvinyl chloride, impregnated with an ionophore can be employed. In the absence of the ionophore, the film is an insulator and no EMF can be measured; when blended with an ionophore, charged ions are bound to the film and a small, measurable current can be induced to flow. Because the ionophore is selective in its affinity, and thus will bind only certain specific ions, such cells are ion selective. Any measurable EMF is due solely to the presence of the bound ions.

The current flowing across the membrane is so small that the actual quantity of the ion or its counterion transported is insignificant. Electrical neutrality of the membrane is maintained either by a reverse flow of hydrogen ions, or by a parallel flow of hydroxyl anions. This anion effect can reduce the specificity of the electrode towards the intended ion and is an interference to be minimized.

A major difficulty in the use of such ion-selective electrodes has been the marked reduction of accuracy and speed of response over time. Further, small changes in ion concentration produce such small changes in EMF that sophisticated voltmeter equipment is required.

It has been known that certain antibiotics, such as valinomycin, have an affect on the electrical properties of phospholipid bilayer membranes (biological membranes), such that these antibiotics solubilize cations within the membrane, in the form of mobile charged couples, thereby providing a "carrier" mechanism by which cations can cross the insulating hydrocarbon interior of the membrane. These complexes carry charge through the membrane such that a voltage differential can be determined between solutions on either side of the membrane.

U.S. Pat. No. 3,562,129, issued to Simon, describes the use of porous membranes impregnated with macrocyclic derivatives of amino and oxy-acids in ion-sensitive electrodes. Materials used to form the membrane are glass frits and other porous membranes. Such electrodes are said to be effective in measuring ion activities.

U.S. Pat. No. 4,053,381, issued to Hamblen, et al., discloses similar technology, and utilizes an ion specific membrane having ion mobility across it.

2.2 Liquid/Liquid Partitioning

Another known application of ionophores in ion determinations is through liquid/liquid partitioning. In this procedure, a hydrophobic ionophore is dissolved in an organic solvent immiscible with water. Eisenman et al., J. Membrane Biol., 1:294-345 (1969) disclose the selective extraction of cations from aqueous solutions into organic solvents by macrotetralide actin antibiotics. This technique involves shaking an organic solvent phase containing the antibiotics with aqueous solutions containing cationic salts of lipid-soluble colored anions, such as picrates and dinitrophenolates. The intensity of color developed in the organic phase is then measured spectrophotometrically to indicate how much salt has been extracted. Phase transfer has also been studied by Dix et al., Angew. Chem. Int. Ed. Engl., 17:857 (1978) and in reviews including Burgermeister et al., Top. Curr. Chem., 69:91 (1977); Yu et al., "Membrane Active Complexones," Elsevier, Amsterdam (1974); and Duncan, "Calcium in Biological Systems," Cambridge University Press (1976).

Sumiyoshi, et al., Talanta, 24, 763–765 (1977) describes a method for determining potassium ion in serum. In this technique serum is deproteinated by trichloroacetic acid and an indicator dye is added and shaken with a solvent such as chloroform containing valinomycin.

Partitioning of a compound between liquids is rapid and effective, as shown by Eisenman, because of the mobility of the ionophore carrier and ions, which allows the transported species to diffuse rapidly away from the interface. Such a mechanism is normally impossible in the solid phase, because of rigidity, immobility and essentially zero diffusion of materials in a solid phase.

2.3 Fluorescent Anions

Yet another approach to the measurement of ion activity in aqueous solutions utilizes fluorescent anions. Feinstein, et al., Proc. Nat. Acad. Sci. U.S.A., 68, 2037–2041 (1971). It is stated that the presence of cation/ionophore complexes in organic solvents is known, but that complex formation in purely aqueous media had theretofore not been detected. Feinstein, et al., demonstrated the existence of such complexes in water through the use of the fluorescent salts 1-anilino-8-naphthalene sulfonate and 2-p-toluidinyl sulfonate. It was found that interaction of the cation/ionophore complexes with the fluorescent dyes produced enhanced fluorescence emission, increased lifetime and polarization, and significant blue-shift at the emission maxima of the fluorescence spectrum. At constant concentrations of ionophore and fluorophore, the intensity of fluorescence emission was found to be a function of cation concentration.

2.4 Chromophore-labeled Ionophore

The ion assay disclosed in U.S. Pat. No. 4,367,072 is primarily directed toward the use of a a chromogenic ionophore, i.e., an ionophore covalently linked to a chromogen. A charged chromogen-ionophore complex, having the same charge as the ion to be determined, is also used. In use, the chromogenic ionophore or charged chromogen-ionophore complex is added to a liquid sample and the color of the solution is monitored spectrophotometrically. Mention is made of incorporating the ionophore into a carrier such as paper, synthetic resin film, silicon oxide, natural or synthetic fibers or metal.

2.5 Multilayer Test Device

Multilayer formats for the determination of analytes by chemical reaction of the analyte with the components in the reagent layer have been disclosed (see, for example, U.S. Pat. No. 3,992,158 to Przybylowicz et al). Kitajima et al. in U.S. Pat. No. 4,356,149 discloses a multilayer test device wherein the reagent layer is composed of a hydrophilic binder and fine hydrophobic particles dispersed in that binder, which particles contain the reagent capable of producing a color change with the component being analyzed. U.S. Pat. No. 4,356,149, to Kitajima et al, is directed toward eliminating layers made necessary by incompatible reagent components. U.S. Pat. No. 4,255,384, to Kitajima et al, concerns a multilayered integrated element for the chemical analysis of blood.

2.7 Summary

To summarize the background of technological developments leading up to the present invention, many methods are known for assaying ions in solution. Instrumental methods include such sophisticated techniques as ion-specific potentiometry, flame photometry and atomic absorption photometry. The use of ionophores which selectively complex with specific ions has led to five basic approaches: ion selective electrodes, liquid/liquid partitioning, fluorescence enhancement, chromophore-labeled ionophore conjugates and test strips. While multilayer test strips are known, none is useful for the determination of ions, as is the present invention.

3. BRIEF DESCRIPTION OF THE DRAWINGS

FIGS. I–VII are graphical representations of the data obtained in Examples 11.2–11.8, respectively.

In Figure I the detection of potassium using Potassium Ionophore I as the ionophore in Example 11.2 is shown.

Figure II is a graphical representation of the data obtained in Example 11.3 in which both Potassium Ionophore I and valinomycin are present in the test means as ionophores.

Figure III depicts the results of Example 11.4 in which equal amounts of Potassium Ionophore II and valinomycin are utilized in the test means.

Figure IV shows the results of using only valinomycin as the ionophore in a potassium test means, as described in Example 11.5.

Figure V shows the results of using dipentyl phthalate as a plasticizer in the test means of Example 11.6.

Data from Example 11.7, in which a test means responsive to sodium ion concentration is described, is portrayed graphically in Figure VI.

Figure VII is a plot of the data obtained in Example 11.8, in which the reporter substance is tetrabromophenolphthalein ethyl ester.

FIG. VIII is a plot of the data obtained in Example 11.10 for serum potassium determinations in which the reporter is 7-decyl MEDPIN.

Figure IX diagrammatically shows possible configurations of a multilayer test device particularly useful for the determination of ion concentration in a whole blood sample. FIG. IXa depicts a supported three layered device; FIG. IXb depicts a supported two layered device.

4. SUMMARY OF THE INVENTION

The present invention resides in the discovery of a new test means for detecting the presence of a specific ion in an aqueous test sample and to determining its concentration. The test means comprises a substantially nonpolar, nonporous carrier matrix which is incorporated with an ionophore capable of selectively forming a complex with the ion under analysis. In addition, the carrier matrix is incorporated with a reporter substance which is capable of producing a detectable response such as change in, or appearance of, color or fluorescence. A test device is composed of a test means affixed to one flat side of an elongated support member, such as plastic film. In the multilayer format a transparent support member is used to prepare a multilayer test device wherein the detectable response is read through the support.

A preferred embodiment is a multilayer test device particularly suited for whole blood determinations. The test means then forms the reagent layer of a multilayer device.

In use the sample is contacted with the test means or multilayer test means, and the presence and/or concentration of the ion is then determined by observing any detectable response produced.

The test means and device of the present invention provide rapid results, sufficient detectable response forming in most instances in at least a few minutes. The multilayer format is particularly useful, as the ion concentration of a whole blood sample can be determined without washing or wiping the device.

5. DEFINITIONS

The following definitions are provided to clarify the scope of the present invention and to enable its formulation and use.

5.1 The term "ionophore" includes molecules capable of selectively forming a complex with a particular ion in a hydrophobic environment to the substantial exclusion of others. For example, the cyclic polyether 2,3-naphtho-1,4,7,10,13-pentaoxacyclopentadeca-2-ene (sometimes known as 2,3-naphtho-15-crown-5 and called Potassium Ionophore I herein) binds selectively to potassium ions in solution to form a cationic complex. Also included in the term are crown ethers, cryptands and podands.

5.2 As used herein, "substantially nonpolar" is intended as meaning that quality of a substance not to exhibit a substantial dipole moment or electrical polarity. In particular, it includes nonionic substances and substances which are dielectric.

5.3 The term "nonporous" is intended to mean substantially impervious to the flow of water. Thus, a nonporous carrier matrix is one which precludes the passage of water through it, one side to the other. For example, a polyvinyl chloride film would be considered for the purposes herein as being nonporous.

5.4 A "reporter substance" is one which is capable of interacting with an ionophore/ion complex to produce a color change or other detectable response. A preferred reporter for the determination of a cation is a neutral compound such as a dye capable of interacting with the ionophore/cation complex causing the reporter to lose a proton and become charged, effecting a change in electron distribution. The change in electron distribution produces a detectable response. The expression "reporter substance" includes phenolic compounds, such as p-nitrophenol, which are relatively colorless in the nonionized state, but which color upon ionization and fluorescent compounds which produce more or less fluorescence upon a change in electron distribution. The reporter substance can also be one which can trigger a detectable response together with other components. For example, the change in electron distribution in the reporter substance caused by interaction with the complex can in turn facilitate the interaction of the reporter with another component which would then produce a detectable response.

5.5 By "interacting" is meant any coaction between a reporter substance and an ionophore/ion complex which leads to a detectable response. An example of the reporter substance interacting with the complex is where the reporter is changed by the complex from a colorless to a colored state, such as in the case of p-nitrophenol.

5.6 The expression "detectable response" is meant herein as a change in, or occurrence of, a parameter in a test means system which is capable of being perceived, either by direct observation or instrumentally, and which is a function of the presence of a specific ion in an aqueous test sample. Some detectable responses are the change in, or appearance of, color, fluorescence, reflectance, pH, chemiluminescence and infrared spectra.

5.7 By the expression "intermediate alkyl" as used herein is meant an alkyl group having from about 5 to about 15 carbon atoms. It includes normal and branched isomers. It can be unsubstituted or substituted, provided any such substitution not interfere with the operation of the presently claimed test means.

5.8 The expression "lower alkyl", as used in the present disclosure, is meant an alkyl moiety containing about 1 to 4 carbon atoms. Included in the meaning of lower alkyl are methyl, ethyl, n-propyl, isopropyl, n-butyl, sec-butyl and tert-butyl. These can be unsubstituted or substituted, provided any such substituents not interfere with the operation of the test means.

5.9 By "pseudohalogen" is meant atoms or groups of atoms which, when attached to an unsaturated or aromatic ring system, affect the electrophilicity or nucleophilicity of the ring system, and/or have an ability to distribute an electrical charge through delocalization or resonance, in a fashion similar to the halogens. Thus, whereas halogen signifies Group VII atoms such as F, Cl, and I, pseudohalogens embrace such moieties as —CN, —SCN, —OCN, —N$_3$, —COR, —COOR, —CONHR, —CF$_3$, —CCl$_3$, —NO$_2$, —SO$_2$CF$_3$, —SO$_2$CH$_3$, and —SO$_2$C$_6$H$_4$CH$_3$, in which R is alkyl or aryl.

6. TEST MEANS

The test means comprises a substantially nonpolar, nonporous carrier matrix incorporated with an ionophore and a reporter substance. When an aqueous test sample contains an ion capable of specifically complexing with the ionophore, the ion can then enter the matrix forming an ionophore/ion complex, which can interact with the reporter substance to produce a detectable response. The test means can form the reagent layer of a multilayer test means.

6.1 The Carrier Matrix

In order for the test means or reagent layer to provide a detectable response solely as a result of the presence of a specific ion, it is necessary that other ions be substantially excluded from entering the carrier matrix. This is required because the ionophore/ion complex formed triggers the detectable response in conjunction with the reporter substance. Accordingly, the carrier matrix must be fabricated from a material which is both nonpolar and nonporous. Exemplary of such materials are films of such polymers as polyvinyl fluoride, polyvinyl chloride, vinyl chloride/vinyl acetate copolymer, vinyl chloride/vinylidene chloride copolymer, vinyl chloride/vinyl acetate/vinyl alcohol terpolymer, vinylidene chloride/acrylonitrile copolymer, and polyurethane. Of course, many other polymeric materials such as silicon polymers available from Dow Corning (e.g. Q3-9595) would be suitable for use in the present invention, and the identification of such materials would be well within the skill of the art, given the present disclosure.

Preferably, incorporated within the polymer film as part of the nonpolar, nonporous carrier matrix are compounds known in the art as plasticizers which are nonvolatile, high boiling liquids, i.e., those having a boiling point of at least about 150° C., ideally at least about 200° C. As shown in the examples suitable liquids include diethylphthalate and dipentylphthalate. Other suitable liquids include tricresylphosphate, dioctylphthalate, tris-2-ethylhexylphosphate, di-2-ethylhexyl sebacate, n-butylacetyl-ricinoleate and nitrophenyl ethers such as 2-nitrophenyl octyl ether, 2-nitrophenyl butyl ether, dibenzyl ether and o-nitrophenyl-2-(1,3,3)-trimethyl-butyl-5,7,7-triethyl octyl ether. Mixtures of these liquids can be used. Such liquids are normally oxygen donors, containing functional groups such as ether, ester, amide and the like or combinations thereof.

The carrier matrix must be nonporous and nonpolar because the ion must not be able to substantially penetrate the matrix unless it is the particular ion for which the ionophore has complexing affinity. The concept of a nonporous matrix, of course, does not exclude microscopic porosity. It is clear from the foregoing remarks as well as the very nature of the invention, that some porosity could be possible, provided the ion-analyte be precluded from permeation of the carrier matrix to a sufficient degree to cause the detectable response to occur in the absence of the ionophore.

The composition of the carrier matrix in this invention is to be carefully distinguished over prior art carriers whereby porous materials such as paper were used. In that type of device, it is required that any test sample to which the device is exposed be capable of permeating the entire reagent area. Such test devices function on entirely different principles from the present one, and a paper carrier matrix is not considered as within the scope of the present invention unless such paper matrix be rendered substantially nonpolar and nonporous, i.e., such as by polymer or wax coating.

Thus, the carrier matrix is one which substantially precludes penetration by the aqueous test sample. Moreover, it is intended that both the ionophore and reporter substance become virtually insoluble in the aqueous test sample due to their being entrapped with the carrier matrix. The requirement of nonporosity of the carrier matrix is to preclude dissolution or leaching of ionophore or the reporter substance, as well as to prevent permeation by test sample components other than the ion-analyte.

6.2 Ionophores

The ionophore element of the present invention is a concept which is broad in scope, as characterized by the definition of the term in paragraph 5.1, supra. It includes multidentate cyclic compounds which contain donor atoms in their cyclic chains. Such multidentate cyclic compounds can be monocyclic or polycyclic. Alternatively, the ionophore can be an open chain containing donor atoms. Thus, included in the term are monocyclic systems ion-specific compounds known as coronands; polycyclic ion-specific compounds known as cryptands; open chain ion specific compounds known as podands; and antibiotic type ionophores such as valinomycin and macrotetralide actins.

6.2.1 Coronands

The coronands are monocyclic compounds which contain donor atoms which are electron rich (or deficient) and which are capable of complexing with particular cations (or anions) because of their unique structures. Included in this term are the crown ethers in which the monocyclic chain contains oxygen as the donor atoms. Other coronands are compounds which contain an assortment of electron rich atoms such as oxygen, sulfur and nitrogen. Because of the unique sizes and geometries of particular coronands, they are adaptable to complexing with various ions. In so complexing, the electron rich atoms, such as the oxygens in a crown ether, orient towards the electron deficient cation. The carbon atom segments of the chain are simultaneously projected in a direction outwards from the ion. Thus, the resultant complex is charged in the center, but is hydrophobic at its perimeter.

6.2.2 Cryptands

The cryptands are the polycyclic analogues of the coronands. Accordingly, they include bicyclic and tricyclic multidentate compounds. In the cryptands, the cyclic arrangement of donor atoms is three dimensional in space, as opposed to the substantially planar configuration of the coronand. A cryptand is capable of virtually enveloping the ion in three dimensional fashion and, hence, is capable of strong bonds to the ion forming the complex. As with coronands, the donor atoms can include such atoms as oxygen, nitrogen and sulfur.

6.2.3 Podands

Ions can also be selectively complexed with noncyclic compounds. For example, a linear chain which contains a regular sequence of electron rich atoms such as oxygen has the capability of associating with positively charged ions to form complexes, not entirely unlike the coronands and cryptands. The main structural difference between podands and the other two types of ionophores is the openness of the structure. Thus, podands can be subcategorized into monopodands, dipodands, tripodands, and so forth. A monopodand, therefore, is a single organic chain containing donor atoms; a dipodand is two such chains attached to a central atoms or group of atoms is capable of variable spacial orientation; and a tripodand is three such chains attached to a central atom or group of atoms. Uncharged podands are preferred ionophores for the determination of sodium and calcium ions.

Simon, et al. in U.S. Pat. No. 3,957,607 discloses dipodands particularly suited to the determination of calcium or barium ions. In the present invention, a preferred ionophore is the tripodand 1,1,1-tris[1'-(2'-oxa-4'-oxo-5'-aza-5'-methyl) dodecanyl]propane referred to herein as Sodium Ionophore I, which was found to be particularly useful in a test means for the determination of sodium ion. In fact, Sodium Ionophore I is 90 times more selective for sodium ions than the dipodand, N,N'-dibenzyl-N,N'-diphenyl-1,2-phenylenedioxydiacetamide. [Guggi, M., Oehme, M., Pretsch, E. and Simon, W., Helv. Chim. Acta., 59:2417 (1976)].

6.2.4 Specific Ionophores

Some of the ionophores which have been found to be especially useful with the instant invention are tabulated herein along with the cations with which they are capable of selectively complexing.

Chemical names for preferred ionophores follow with their structures. Common names assigned for use herein are noted in brackets.

| Ionophore | Cation |
|---|---|
| 1,1,1-tris[1'-(2'-oxa-4'-oxo-5'-aza-5'-methyl)dodecanyl]propane | Na+ |

[Sodium Ionophore I]

| Ionophore | Cation |
|---|---|
| N,N'—dibenzyl-N,N'—diphenyl-1,2-phenylenedioxydiacetamide | Na+ |

[Sodium Ionophore II]

| Ionophore | Cation |
|---|---|
| 6,7,9,10,18,19-hexahydro-17-n-butyl dibenzo[b,k] [1,4,7,10,13]pentaoxa-cyclohexadecane-18-yl-oxyacetic acid | Na+ |

[Sodium Ionophore III]

| Ionophore | Cation |
|---|---|
| 2,3-naphtho-1,4,7,10,13-pentaoxa-cyclopentadeca-2-ene | K+ |

[Potassium Ionophore I]

| Ionophore | Cation |
|---|---|
| N,N'—diheptyl-N,N',5,5-tetramethyl-3,7-dioxanonane diamide | Li+ |

[Lithium Ionophore I]

| Ionophore | Cation |
|---|---|
| N,N'—diheptyl-5,5-dimethyl-N,N'—di(3-oxapentyl)-3,7-dioxanane diamide | Li+ |

[Lithium Ionophore II]

| Ionophore | Cation |
|---|---|
| cis-N,N,N',N'—tetraisobutyl-1,2-cyclohexane dicarboxamide | Li+ |

| Ionophore | Cation |
|---|---|
| 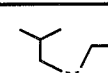 [CDA] | |

| Ionophore | Cation |
|---|---|
| diethyl-N,N'—[(4R,5R)—4,5-dimethyl-1,8-dioxo-3,6-dioxaoctamethylene]-bis(12-methylaminododecanoate) | Ca$^{++}$ |

[Calcium Ionophore]

Other ionophores which are useful in the present invention include those listed below:

| Ionophore | Cation |
|---|---|
| 15-crown-5 | Na$^+$, K$^+$ |
| Valinomycin | K$^+$ |
| 4,7,13,16,21,24-hexaoxa-1,10-diaza-bicyclo [8,8,8]hexacosane (Kryptofix ® 222) | K$^+$ |
| Dibenzo-18-crown-6 | K$^+$ |
| Dicylcohexano-18-crown-6 | K$^+$ |
| 4,7,13,18-tetraoxa-1,10-diaza-bicylco[8,5,5]eicosane (Kryptofix ® 211) | Li$^+$ |
| 12-crown-4 | Li$^+$ |
| N,N'—diheptyl-N,N'—dimethyl 1,4-butanediamide | Mg$^{++}$ |

Kryptofix ® is a trademark of E. Merck, Darmstadt, West Germany.

Although these specific ionophores were used advantageously in the test means of the present invention, other ionophores or mixtures thereof, can also be used. It has been shown that a 1:1 weight to weight ratio of valinomycin to Potassium Ionophore I exhibits an unexpectedly enhanced response as measured by the ratio of the slope of the dose response to the intercept (i.e., the blank). In particular, ionophores which contain ionizable groups, such as Sodium Ionophore III, can be substituted in the formulation, so long as they have sufficient ion-analyte specificity.

6.3 The Reporter Substance

Given the presence of the ion of interest in the test solution, it is the reporter substance which provides the detectable response as a result of its interacting with the ionophore/ion complex. The reporter substance can range in composition from a single compound which can ionize in response to the formation of the ionophore/ion complex, to a mixture of reactive species which produce a detectable product when their reaction chain is triggered by the complex. Thus, it can be seen that when no ion-analyte is present, the reporter substance remains dormant and no detectable response is observed. Alternatively, when the particular ion of interest is present, it is enabled by the ionophore to enter the carrier matrix to form a complex, which complex interacts with the reporter substance and induces it to undergo a detectable change.

In the case where the reporter is a single compound, it can include a dissociable group such that upon dissociation the ionic species formed exhibits a color different from the undissociated species. For the determination of a cation, a particularly preferred reporter is a neutral compound having a dissociable proton such that upon interaction of the ionophore/cation complex with the reporter, the reporter loses a proton. This proton loss causes a change in, or appearance of, a detectable response in the matrix. Tetrabromophenolphthalein alkyl esters are useful reporters. Phenolic compounds such as p-nitrophenol, are relatively colorless in the nonionized state but are colored upon ionization can also be useful. Other compounds, such as those which produce more or less fluorescence upon a change in electron distribution, can also be used. Classes of fluorescent indicators and their derivatives which are useful in this invention include derivatives of fluorescein, especially fluorescein esters, 7-hydroxy coumarins, resorufins, pyrene-3-ols and flavones.

The reporter substance can also be one which can trigger a detectable response together with other components. For example, a reaction sequence useful as the reporter substance is one which involves the dissociation of a proton from a phenol, thus initiating a coupling reaction to form a colored product. The so-called Gibbs Reaction is typical of such a reaction sequence, in which 2,5-cyclohexadiene-1-one-2,6-dihalo-4-haloimine (I) couples with a phenol (II) to form a colored reaction product (III).

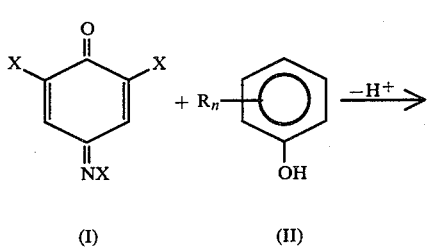

(I)    (II)

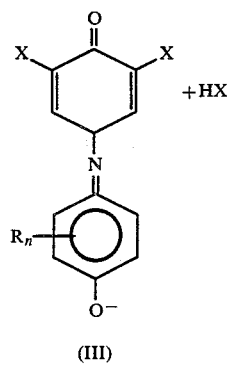

(III)

In this reaction sequence R, same or different, can be any 2, 3, 5 or 6-position substitutent, or multiple substituents thereof, which will not hinder the overall reaction sequence, and n is 1 to 4. Thus R is H, lower or intermediate alkyl or aryl, or R can form a fused ring system at either the 2,3- or 5,6-positions. The X, same or different, is halogen such as F, Cl, Br and I, or X can be a pseudohalogen. It is preferred that 2 and 6 position substituents be the same. The trichlorocompound is particularly preferred. This reporter substance can be utilized by incorporating compounds having the structures (I) and (II) directly with the carrier matrix.

Still another utilization of the Gibbs chemistry involves compounds having a structure such as (III) in its nonionized form. The formation of the ionophore/ion complex results in an interaction such that reporter substance (III) yields observable color in and of itself. This phenomenon can be thought of as proceeding in accordance with the following reaction sequence and resonance structures:

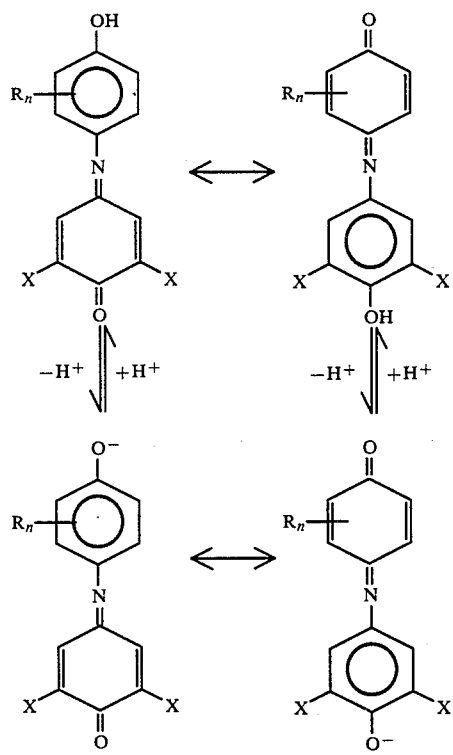

in which each R, same or different, is lower alkyl or intermediate alkyl, aryl, or a fused ring system at the 2,3- or 5,6-positions, n is 0 to 4 and X is as defined above. Especially preferred is a compound having the structure

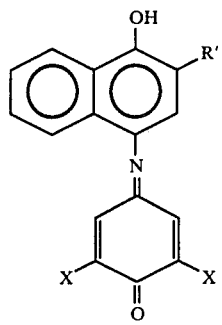

in which R' is H or lower alkyl and X is a halogen or pseudohalogen group as defined in sections 5.8 and 5.9, respectively. The case in which R' is methyl and each X is a chloro group has been found especially suitable to the present invention.

Yet another preferred reporter substance is a compound having the structure

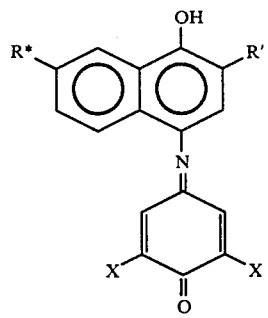

In which R* is an intermediate alkyl group, i.e., having 5 to 15 carbon atoms, and in which R' is H or lower alkyl and X is halogen or pseudohalogen. Compounds such as these have been found to be especially resistant to possible interference due to the presence of serum albumin in the test sample. Preferred among these type of reporter substances is 7-(n-decyl)-2-methyl-4-(3',5' dichlorophen-4'- one)indonaphthol (referred to herein as 7-decyl-MEDPIN) in which R* is n-decyl, X is a chloro group and R' is methyl. More detailed information on the use and preparation of such compounds can be found in U.S. patent application Nos. 493,951 and 431,981, both of which are assigned to the present assignee and are incorporated herein by reference.

In general, neutral reporters which have a dissociable proton are preferred for the determination of a cation.

6.4 Optional Components (Reagent Layer)

The test means or reagent layer can optionally include photochemical stabilizers, thickeners, preservatives and so forth, provided they do not interefere with the production of the detectable response. Given the present disclosure, the choice of such components is well within the skill of those knowledgeable in the art.

In the single layer format, when instrumental reading by reflectance is used, it is advantageous to incorporate light scattering centers with the carrier matrix. The use of such centers effectively increases the precision of the assay by reducing the effect of variations in film thickness. Light scattering centers can be produced by incorporating insoluble inorganic particles such as titanium dioxide particles or equivalents such as barium sulfate, calcium carbonate, aluminum oxide, magnesium oxide, zinc oxide, lead oxide, microcrystalline cellulose or talc. A working range for incorporation of titanium dioxide particles is up to about 40% (weight percent) of the coating emulsion; a preferred range is from about 0.5 to about 15 weight percent of coating emulsion. A particle size of less than one micron is preferred.

7. CONCENTRATION RANGES OF TEST MEANS COMPONENTS

The concentrations of the test means components are not critical to the invention provided that the concentrations of the ionophore and reporter substance are sufficient to produce the desired detectable response. For qualitative results neither the concentration of the ionophore nor the concentration of the reporter substance is tied to the concentration range of the ion-analyte to be determined.

Determination of optimum concentrations is within the ability of one skilled in the art, given the present disclosure. However, the following guidelines are provided. It is preferable that the ionophore be present in molar excess over the reporter substance (i.e., greater than 1:1 molar ratio, ionophore:reporter substance). Working concentrations of the ionophore can range from 2 gm/L to saturation.

The working and preferred concentration ranges for a test means responsive to potassium ion are given below. Preferred ranges are given for the determination of serum potassium by reflectance on an Ames SER-ALYZER ® reflectance photometer. These concentrations, which can be used as a starting point for the determination of useful concentration ranges for the determination of other ions with other ionophores and reporters, are given below. The concentrations of ionophore and reporter refer to concentration in the volume of organic solvent used, other concentrations are defined as grams per 100 grams of solution. The film wet emulsion thickness for the test means (or reagent layer of a multilayer test device) can be from about 25 microns to about 500 microns with the preferred wet emulsion film thickness being from about 150 microns to about 200 microns. The preferred weight to weight ratio of polymer to plasticizer is from about 1:1.5 to 1:3.

|  | working | preferred |
|---|---|---|
| I. Test Means (Reagent Layer) | | |
| Film thickness | 25–500 microns | 150–200 microns |
| Ionophore | 10–500 mM | 80–160 mM |
| Reporter | 10–120 mM | 30–60 mM |
| Light Scattering centers (optional) | 0–40% | 0.5–15% |
| Polymer | 5–25% w/w | 5–25% w/w |
| Plasticizers | 8–50% w/w | 8–50% w/w |
| II. Optional Multilayers | | |
| 1. Reflecting layer | | |
| Titanium dioxide | 5–40% | 15–40% |
| Gelatin | 1–6% | 2–8% |
| Interferant removal substance (optional) | 0–30 gm/L | 10–20 gm/L |
| Buffer (optional) | 0–0.5 M | 0.2–0.5 M |
| Sodium Chloride (optional) | 0–0.6 M | 0.05–0.15 M |
| Wetting substance (optional) | 0–3 gm/L | 1–2 gm/L |
| Dry coating weight | 2.5–75 gm/m² | 10–25 gm/m² |
| 2. Opacifying layer | | |
| Carbon black | 3–30% | 7–15% |
| Gelatin | 1.0–12% | 1.5–6% |
| Interferent removal substance (optional) | 0–30 gm/L | 10–20 gm/L |
| Buffer (optional) | 0–0.5 M | 0.2–0.5 M |
| Sodium Chloride (optional) | 0–0.6 M | 0.5–0.15 M |
| Wetting substance (optional) | 0–3 gm/L | 1–2 gm/L |
| Film thickness (wet) | 10–50 microns | 15–35 microns |

Working and preferred ranges for additional layers used to prepare a multilayer test means or device particularly suited for whole blood electrolyte determinations are included in the above table for easy reference. The composition and use of such additional layers will be described more completely later in the specification.

8. THE SINGLE LAYER TEST DEVICE

The test means can be used by itself, prepared in a multilayer format and/or mounted at one end of an elongated support member The other end then serves as a handle. Such a test device can be held at the handle end, while the other end bearing the test means or multilayer test means is contacted with the test sample.

Useful materials for the support member include films of a myriad of plastics or polymers. Examples include such polymeric materials such as cellulose acetate, polyethylene terephthalate, polycarbonates and polystyrene. The support can be opaque or it can transmit light or other energy. When the detectable response is fluorescence or when a coating is placed over the upper surface of the single layer test device to allow the sample to be wiped off, the test device can be read through the support material. Preferred supports include transparent materials capable of transmitting electromagnetic radiation of a wavelength in the range of about 200 nanometers (nm) to 900 nm. The support need not, of course, transmit over the entire 200–900 nm region, although for fluorometric detection of analytical results it is desirable that the support be transparent over a band wider than, or at least equal to, the absorption and emission spectra of the fluorescent materials used for detection. It may also be desirable to have a support that transmits one or more narrow wavelength bands and is opaque to adjacent wavelength bands. This could be accomplished, for example, by impregnating or coating the support with one or more colorants having suitable absorption characteristics.

To prepare a single layer test device of the present invention, a solution of the requisite ingredients is prepared in a suitable organic solvent. Suitable organic solvents include cyclohexanone, tetrahydrofuran and acetone. Many others, of course, can be used. The solution is coated onto a support such as plastic and dried. The dried film can then either be peeled off, affixed to an elongated support and cut into a small rectangle member having a upper substantially flat face, such as an oblong piece of polystyrene film; or the coated film/plastic combination can be cut and affixed to a support member suitable for a handle. In either case the test means piece is affixed to the flat face at one end of the support, leaving the other end of the polystryene to serve as a convenient handle.

The test means can be affixed by any means compatible with the intended use. A preferred method is by using a double faced adhesive tape between the test means square and the support member. Double sided adhesive tapes are available from 3M Company, St. Paul, Minn.

10. USE OF THE SINGLE LAYER TEST DEVICE

The test means and device of the present invention can be adapted for use in carrying out a wide variety of chemical analyses, not only in the field of clinical chemistry, but in chemical research and chemical process control laboratories. They are well suited for use in clinical testing of body fluids, such as blood, serum, cerebrospinal fluid and urine, since in this work a large number of repetitive tests are frequently conducted, and test results are often needed a very short time after the sample is taken. A preferred use is the testing of cations such as $K^+$, $Na^+$, $Li^+$, or $Mg^{++}$. In the field of blood analysis, for example, the invention can be adapted for use in carrying out quantitative analyses for many of the blood electrolytes of clinical interest. The present invention provides a single layer test particularly useful for the determination of serum potassium which requires measurements of high sensitivity and high precision.

The test means (and test device) is used by contacting it with the test sample for a sufficient period of time. In the case of urine testing merely dipping the test means (or device) into the sample is sufficient. Although it is usually unnecessary to remove excess sample, in some cases, such as whole blood samples, it is desirable to remove any excess by wiping or blotting.

If the ion under analysis is present in the test sample, the ionophore/ion complex will interact with the reporter substance, and a response will be detectable. Where the reporter substance is a dissociable substance producing a colored compound different from the undissociated compound, an observable color (change) will form in the test means which can be instrumentally monitored from either side of the device when a transparent support member is used. Where the reporter substance is a fluorophore such as fluorescein or its derivatives, a fluorescence spectrophotometer can be utilized to measure the detectable response formed in the test means (here, the appearance of or change in fluorescence). Other techniques useful in observing a detectable response include reflectance spectrophotometry, absorption spectrophotometry and light transmission measurements.

Various calibration techniques are applicable as a control for the analysis. For example, a sample of analyte standard solution can be applied to a separate test means as a comparison or to permit the use of differential measurements in the analysis. Test means (or devices) can be formulated wich are suitable for semiquantitative visual determinations when an appropriate color chart is supplied.

10. MULTILAYER FORMAT

The test means can form the reagent layer containing the ionophore and reporter substance of a multilayer format for the determination of an ion in an aqueous fluid sample.

A preferred multilayer device can be prepared by the addition of a reflecting layer disposed on the top of the reagent layer and optionally an opacifying layer disposed on top of the reflecting layer. The use of these additional layers is particularly useful for colored samples such as whole blood, as the reflective or opacifying layer(s) permit reading of ion concentration from beneath the reagent layer without interference by the inherent color of the sample.

10.1 Reflecting Layer

The reflecting layer contains a material or materials which act as light scattering centers providing a background to aid the user in determining the detectable response in the reagent layer of the device. In a preferred embodiment for whole blood determinations, the purpose of the reflecting layer is to screen the color of the red blood cells in the sample being tested from the color change to be observed by the user. The preferred material for "screening purposes" is titanium dioxide. However, other materials can be used, for example, barium sulfate, calcium carbonate, aluminum oxide, magnesium oxide, zinc oxide, lead oxide, talc and microcrystalline cellulose. Such a material is contained in the reflecting layer in an amount of 15 to 50 weight percent, preferably 18 to 40 weight percent, based on the total weight of the reflecting layer. Such materials generally have a particle size of less than one micron. The materials generally have a dry coating weight of 2.5 to 75 gm/m$^2$, preferably 10 to 25 gm/m$^2$.

In addition to the aforesaid materials, the reflecting layer usually contains a hydrophilic substance. Useful hydrophilic substances include water soluble polymers which in their dry state exhibit a marked wettability by aqueous media, such as gelatin, poly(vinyl alcohol), poly(propyleneimine), carrageen, copolymers of acrylic acid and alginic acid. A preferred substance is gelatin which is contained in an amount of 2 to 8 weight percent, preferably 1 to 6 weight percent, based on the total weight of the reflecting layer. The remainder of the reflecting layer is usually water.

Additionally, the reflecting layer can contain one or more wetting agents (detergents) and/or one or more suspending agents. A nonlimiting example of a wetting agent that can be employed in the reflecting layer is Triton® X-100. For example, in a test involving the determination of potassium, 0 to 0.5 weight percent Triton® X-100 can be utilized.

Nonlimiting examples of suspending agents for use in the reflecting layer include gelatin, alginate and hydrophillic urethanes.

The reflecting layer has a dry coating weight in the range of about 2.5 to 75 grams per square meter, preferably 10 to 25 grams per square meter.

To prepare a multilayered device, the reflecting layer is coated on top of the reagent layer and dried at about 40° C. for about 10 minutes.

9.2 Opacifying Layer

In a preferred embodiment, an opacifying layer is deposed on top of the reflecting layer, i.e., the opacifying layer is optional.

The opacifying layer has a wet layer thickness (thickness when applied) of 10 to 50 microns, preferably 15 to 35 microns. The opacifying layer contains substantially inert particles for imparting an opaque appearance to the layer. Such particles can be, for example, carbon black particles.

A multilayer device containing an opacifying layer is prepared by spreading the opacifying layer on top of the reflecting layer and drying the whole device again at about 40° C. for about 10 minutes.

9.3 Optional Components for Reflecting and/or Opacifying Layers

The reflecting and/or opacifying layers can contain optional components such as a buffer, an interferant removal substance or sodium chloride.

9.3.1 Buffer

A buffer or combination of buffers can be incorporated with the reflecting and/or opacifying layer. Upon contact with an aqueous fluid sample, the buffer redissolves into the aqueous phase thus created, raising or lowering the pH to the desired level for the generation of the detectable response to proceed. With preferred reporters capable of losing a dissociable proton upon interaction with the ionophore/ion complex, the buffer maintains a suitable pH for the reaction to proceed. Prebuffering allows the multilayer test device to be used with unbuffered and undiluted samples such as sera or whole blood Suitable buffers include bis[2-hydroxyethyl]iminotris[hydroxymethyl]methane;1,3-bis[tris-(hydroxymethyl)methylamino]propane, N,N-bis-(2-hydroxyethyl)glycine, tris(hydroxymethyl)aminomethane, N-[2-acetamido]2-iminodiacetic acid; N-2-hydroxyethylpiperazine-N', 3-propanesulfonic acid; 3[N-tris(hydroxymethyl)methylamino-2-hydroxypropanesulfonic acid; tetramethylammonium borate; 3-(cyclohexylamino)-propane sulfonic acid and tetramethylammonium phosphate.

The preferred pH range depends on the reporter substance. Therefore, the choice of the buffer is determined by the reporter substance used and to some extent by the desired detectable response. For example, when 7-decyl MEDPIN is used as the reporter, the preferred pH range is from 6 to 8.5. However, when a reporter substance having a higher pKa for the dissociable proton is used, a higher pH range will be preferred. Similarly when a reporter having a lower pKa for the dissociable proton is used, a lower pH range will be preferred. When the detectable response is a color change, the buffer can influence the degree of such detectable response, and a particular buffer can be chosen for color intensity optimization. For example, the useful pH range for the reporter, 7-decyl MEDPIN, occurs from about pH 6 to 8.5 where the color change is from orange to blue. A higher pH, pH 8.5-10, gives shades of dark blue which are difficult to distinguish visually, and a lower pH, pH 5-6, gives shades of pale yellow, also difficult to distinguish visually. Both pH extremes could be used with instrumental analysis, although the best instrumental precision occurs at the pH range of from about 6 to 8.5. Determination of a suitable pH is a routine laboratory experiment.

9.3.2 Interferant Removal Substance

Body fluids normally contain many cations, such as sodium ion ($Na^+$), potassium ion ($K^+$), calcium ion ($Ca^{++}$) and magnesium on ($Mg^{++}$). Although the ionophore will usually be chosen for its selectivity for the desired analyte-ion, in some cases the presence of other cations could interfere with the coaction of the ionophore with the desired analyte-ion. For example, Sodium Ionophore I will bind sodium ion in preference to calcium ion in a ratio of approximately 4 to 1. In samples where the ratio of sodium ion to calcium ion is less than 4 to 1, it may be necessary to prevent the interaction of calcium ion with the ionophore to ensure the proper relationship between sodium ion concentration and the detectable response. An interferant removal substance can be provided to obviate this problem.

An interferant removal substance can be incorporated into the reflecting and/or opacifying layers. In a preferred embodiment, the removal substance is designed to interact with an interfering cation so as to keep it in the aqueous phase formed by contact with the aqueous fluid sample, or otherwise prevent cation interaction with the ionophore in the nonporous nonpolar matrix. For example, ethylenediamine tetraacetic acid (EDTA) and ethyleneglycol bis(aminoethyl)tetraacetic acid (EGTA) are water soluble compounds which form complexes with divalent cations, such as calcium ion. If EDTA is incorporated with the reflecting and/or opacifying layers of a multilayer test device for the determination of sodium ion, EDTA will preferentially bind calcium ion on contact with an aqueous sample containing sodium and calcium ions. The bound calcium ion will not substantially interfere with the formation of the ionophore/sodium ion complex in the nonpolar, nonporous reagent layer. In addition, ionophores can be used to remove interfering cations if they are specific for the interfering ion and are water soluble or are modified chemically to increase their water solubility without decreasing their ability to interact with the interferant. For example, Sodium Ionophore III can be modified by the addition of solubilizing groups, such as ($-SO_3H$) groups, to the benzene rings to increase its water solubility without decreasing its ability to interact with sodium ion. Other compounds such as uramildiacetic acid and trans-1,2-diaminocyclohexane-N,N,N',N'-tetraacetic acid can also be used advantageously.

9.3.3 Sodium Chloride Addition to Decrease Hematocrit Dependence

Sodium Chloride can be incorporated with the reflecting and or opacifying layers. The addition of approximately 0.1 to 0.2M sodium chloride has been found to be sufficient to obviate the hematocrit dependence otherwise seen with whole blood potassium tests. The addition of salt is advantageous in the multilayer format preferred for whole blood electrolyte determinations.

9.4 Description of Multilayer Test Device

A multilayered device 12 in accordance with the present invention is depicted in FIG. IXa and IXb. FIG. IXb shows a two layered multilayered device 12, composed of a transparent support layer 14 on top of which is disposed a reagent layer 16. A reflecting layer 18 is disposed on top of the reagent layer 16. FIG. IXa shows a three layered device in which an opacifying layer 20 is disposed on top of reflecting layer 18. A sample 22 is placed on top layer. The color development is read from the bottom of layer 14 by the human eye or using a device, e.g., a Glucometer ® reflectance photometer which has been adapted for ion determinations.

9.5 Use of Multilayer Device

In using the multilayer device, a sample, such as whole blood, is applied on top of the uppermost layer, i.e., the reflecting layer if no opacifying layer is employed, or the opacifying layer and the detectable response is read from below through a transparent support. Reading can be accomplished either visually when a suitable color chart is supplied or instrumentally. The particular examples disclosed are designed to be read by reflectance.

The presence of the added reflecting layer or reflecting and opacifying layers effectively seal the reagent layer from the outside environment. Accordingly, the multilayer device protects the reagent in that without the added layer(s), the reagent would be exposed and, therefore, susceptible to damage due to mechanical contact. The presence of the added layer(s) also serve to prolong the stability of the generated color.

In addition, in the case where potassium is sought to be detected (for example, with valinomycin as the ionophore), the presence of the additional layer(s) allow for improved visual discrimination between different concentration levels.

The use of the reflecting layer or reflecting and opacifying layers also provides a blocking mechanism to cells, proteins and other macromolecules, thus permitting the use of whole blood in tests. In addition due to the filtration capabilities of these layers, a multilayer test device for calcium measures only ionized calcium (unbound calcium) as bound calcium does not reach the reagent layer. Single and multilayer calcium tests can be used to provide information on total versus ionized calcium.

11. EXAMPLES

Abbreviations used in the examples are as follows:
Square brackets, [ ], are used to designate ion concentration in millimoles per liter (mM) in the linear regression equations. All percent concentrations are given in weight per deciliter unless otherwise indicated.

| Temperature: °C. | degrees Centigrade |
|---|---|
| Length: cm | centimeters |
| Thickness: mil | 1 mil is equal to 25.4 microns |
| Weight: | |
| gm | gram |
| mg | milligram |
| Volume: | |
| dL | deciliter |
| mL | milliliter |
| µL | microliter |
| L | liter |
| Concentration: | |
| mM | millimolar (millimoles per liter) |
| M | molar (moles per liter) |
| % w/v | percent weight per deciliter |
| % v/v | percent volume per deciliter |
| Ions: | |
| $Na^+$ | sodium ion |
| $K^+$ | potassium ion |
| $Li^+$ | lithium ion |
| $Ca^{++}$ | calcium ion |
| $Mg^{++}$ | magnesium ion |

Abbreviations for chemical components used are given below. The ionophore designations are assigned for convenience only. The name is usually based on the principal ion the ionophore was used to determine. However, the ionophores commonly respond, to varying lesser degrees, to other ions. (Structures of preferred ionophores are given in Section 6.3.4);

| Ionophores | |
|---|---|
| Sodium Ionophore I | 1,1,1-tris[1'-(2'-oxa-4'-oxo-5'-aza-5'-methyl)-dodecanyl]propane |
| Sodium Ionophore II | N,N'—dibenzyl-N,N'—diphenyl-1,2-phenyl-enedioxydiacetamide |
| Sodium Ionophore III | 6,7,9,10,18,19-hexahydro-17-n-butyl-dibenzo[b,k] [1,4,7,10,13]pentaoxacycloxadecane 18-yl-oxyacetic acid |
| Potassium Ionophore I | 2,3-naphtho-1,4,7,10,13-pentaoxacyclopentadeca-2-ene |
| Lithium Ionophore I | N,N'—diheptyl-N,N'—5,5-tetramethyl-3,7-dioxanonane diamide |
| Lithium Ionophore II | N,N'—diheptyl-5,5-dimethyl-N,N'—di-(3-oxapentyl)-3,7-dioxanonane diamide |
| CDA | cis-N,N,N',N'—tetra-isobutyl-1,2-cyclohexane dicarboxamide |
| Calcium Ionophore | diethyl-N,N'—[(4R,5R)—4,5-dimethyl-1,8-dioxo-3,6-dioxaoctamethylene]bis(12-methylaminododecanoate) |
| Hydrophobic Substance | |
| NPOE | 2-nitrophenyl octyl ether |
| NPBE | 2-nitrophenyl butyl ether |
| CDA | cis-N,N,N',N'—tetra-isobutyl-1,2-cyclohexane dicarboxamide |

[Those below all obtained from Aldrich Chemical Co., Milwaukee, WI. unless otherwise noted]

| PVC | polyvinyl chloride |
|---|---|
| (low MW) | low molecular weight |
| (very low MW) | very low molecular weight |
| VdC/VC | vinylidene chloride/vinyl chloride copolymer (Scientific Polymer Products, Inc., Ontario, N.Y.) |
| VdC/AN | vinylidene chloride/acrylonitrile copolymer (Scientific Polymer Products, Inc. Ontario, N.Y.) |
| PC - I | polycarbonate (molecular weight 20,000 to 25,000) |
| PC - II | polycarbonate (molecular weight 33,800) |
| PC - III | polycarbonate (molecular weight 38,100) |
| Reporter Substance | |
| 7-decyl MEDPIN | 7-(n-decyl)-2-methyl-4-(3',5'-dichlorophen-4'-one)-indonaphthol |
| Buffering Substance | |
| Bis-Tris | bis[2-hydroxyethyl]-imino-tris(hydroxymethyl)methane |
| Bis-Tris propane | 1,3-bis[tris(hydroxymethyl)methylamino]-propane |
| Tris | tris(hydroxymethyl)-aminomethane |
| Tris-Cl | tris(hydroxymethyl)-aminomethane hydrochloride |
| ADA | N—[2-acetamido]-2-iminodiacetic acid |
| HEPPS | N—2-hydroxyethylpiperazine-N',3-propanesulfonic acid |
| Bicine | N,N—bis[2-hydroxyethyl] glycine |
| TMA borate | tetramethylammonium |

| | -continued | |
|---|---|---|
| TMA phosphate | borate tetramethylammonium phosphate | |
| TAPSO | 3[N—tris(hydroxy-methyl)methylamino]-2-hydroxypropane sulfonic acid (obtained from P.L. Biochemicals, Inc., Milwaukee, WI.) | |
| CAPS | 3-(cyclohexylamino)-propane sulfonic acid | |
| Miscellaneous | | |
| THF | tetrahydrofuran | |
| EDTA | ethylenediamine tetraacetic acid | |
| EGTA | ethylene glycol-bis(aminoethyl)-tetraacetic acid (G. Fredrick Smith Chemical O., Columbus OH) | |
| Triton ® X-100 | polyethylene glycol-p-isooctylphenyl ether (Sigma Chemical Co., St. Louis, MO.) | |
| Zonyl ® FSK | 2-O—acetoxy-3-(perfluoro-alkyl)-N—carboxymethyl-N,N—dimethylpropyl-amine (Dupont Chemical Co., Wilmington, Del.) | |
| Zonyl ® FSN | polyethylene glycol-1-(2-perfluoroalkyl)-ethyl ether (DuPont Chemical Co., Wilmington Del.) | |
| Zonyl ® FSB | N—perfluoroalkyl-N—carboxyethyl-N,N—dimethylamine (DuPont Chemical Co., Wilmington Del.) | |
| Zwittergent ® 3-10 | n-decyl-N,N—dimethyl-3-ammonio-1-propane-sulfonate (Calbiochem-Behring, San Diego, CA.) | |
| Brij ® 358P | polyoxyethylene ethers of fatty alcohols (ICI United States, Inc., Wilmington, Del.) | |
| Na DDBS | Sodium dodecyl benzene sulfonate | |

This invention will now be illustrated, but is not intended to be limited, by the following examples.

11.1 Preparation of 7-(η-Decyl)-2-methyl-4-(3′,5′-dichlorophen-4′-one)-indonaphthol The captioned compound (hereafter 7-decyl-MED-PIN) was prepared for use as a reporter substance in the present test means and test device. The reaction pathway is depicted in the following sequence, in which R* is η-decyl.

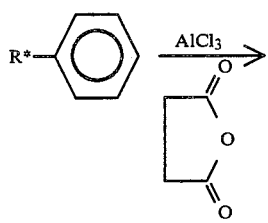

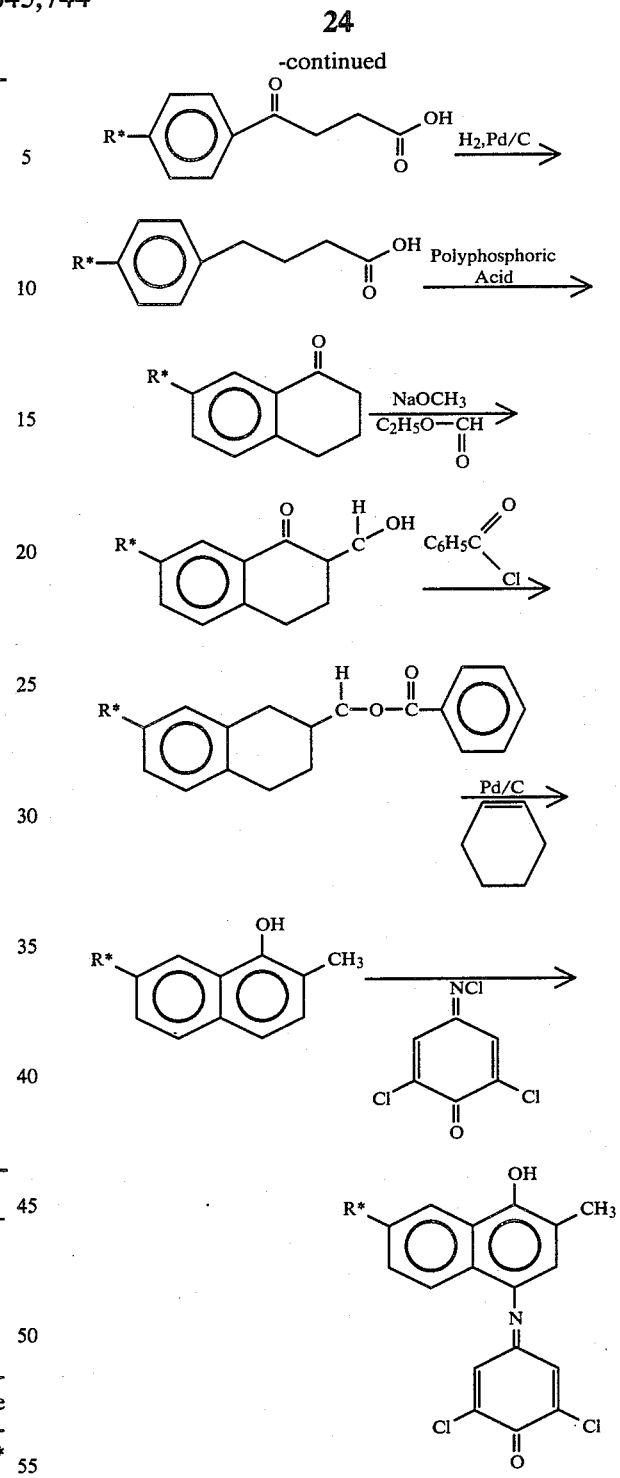

Preparation of β-(p-η-Decylbenzoyl)-propionic Acid

A mixture of 26.2 grams (gm) phenyl-η-decane (1.2 mole), 120 gm succinic anhydride (1.2 mole) and 360 mililiters (mL) nitroethane in an 5 liter (L) three-necked flask equipped with HCl outlet and mechanical stirrer was cooled to 0° C. in an ice-bath. To this mixture 360 gm AlCl₃ (2.7 moles) was added slowly over ½ hour with stirring. Evolution of HCl was observed when about half of the AlCl₃ was added. After the addition, the ice bath was removed, the reaction mixture was allowed to stand at room temperature (RT) for 5 minutes. The mixture was then heated over a steam bath. The heating and stirring was continued until the vigorous evolution of HCl ceased (about 30 minutes). The reaction was cooled in an ice bath while 2 L of ice water was added followed by 600 mL of concentrated HCl. This was stirred at RT for 2 hours until all the dark brown solid was hydrolyzed. The insoluble product was recovered by filtration. The solid was then recrystallized twice with acetic acid (250 mL each time) to give about 320 gm (85% yield) of product (dried in vaccum over KOH). TLC: Rf 0.43 in 1:1 (v/v) ethylacetate:toluene (silica gel plate).

Analysis: Calculated for $C_{20}H_{30}O_3$: C, 75.42; H, 9.50. Found: C, 76.02; H, 9.89.

Preparation of 4-(p-η-decyl-phenyl)-butyric acid

Twenty grams of Pd/C (palladium-saturated carbon obtained from Aldrich Chemical Co., catalogue No. 20,569-9) and β-(p-η-decyl-benzoyl)-propionic acid (150 gm 0.47 moles) were mixed with acetic acid (350 mL) in a 1 liter Paar bomb. The reaction was started at 50 psi (pounds per square inch) $H_2$ pressure and 50° C. A sudden increase in temperature accompanied by a drop in $H_2$ volume was observed. Thin layer chromatography on the reaction mixture indicated complete reaction. The catalyst was removed by glass fiber filtration while hot. The filtrate was allowed to crystallize at room temperature. The crystalline product was removed by filtration. Product which formed after the filtrate was chilled was also recovered. The total yield was 100 gm (68%) after drying under a vacuum over KOH. The melting point was 67°-69° C.

TLC: Rf 0.68 in 1:1 (v/v) ethylacetate:toluene (silica gel plate)

Analysis Calculated for: $C_{20}H_{32}O_2$: C, 78.90; H, 10.50. Found: C, 78.39; H, 10.70.

Preparation of 7-η-Decyl-1-tetralone

A mixture of p-decyl-phenyl butyric acid (30 gm, 98.7 mmoles) and polyphosphoric acid (150 gm) was heated in an oil bath until all solid was melted. The heating was elevated to an internal temperature of 150° C. and the mixture was stirred vigorously for 30 minutes. The reaction was then cooled to room temperature and treated with 300 mL ice water and 150 mL ethyl ether. After the mixture was stirred for 30 minutes at room temperature, the aqueous layer was separated and washed twice with 150 mL ethyl ether. The combined organic phases were washed with 150 mL saturated aqueous sodium chloride. Ether was removed by evaporation and the residue was distilled on a Kugelrohr distillation apparatus (Aldrich Chemical Co., Milwaukee, Wis.). The product has a boiling point of 190°-200° C./0.1 mm Hg. The yield was 11 gm (39%) of pale yellow oil.

TLC: Rf - 0.34 in toluene (silica gel plates)

Analysis Calculated for: $C_{20}H_{30}O$: C, 83.90; H, 10.70. Found: C, 85.63 H, 10.83.

Preparation of 2-Hydroxymethylene-7-n-decyl-1-tetralone

A mixture of sodium methoxide (5.4 gm, 40.5 moles), ethyl formate (7.4 gm, 100 mmoles) and 100 mL dry toluene was cooled in an ice bath under inert atomosphere nitrogen. A solution of the 7-decyl-tetralone (11.5 gm, 40 mmoles) in 100 mL dry toluene was added with rapid stirring. The ice bath was removed and the reaction was stirred at room temperature for 4 hours. The reaction mixture was treated with 100 mL water and 100 mL 6N HCl. The organic layer was separated and washed twice with 50 mL saturated sodium chloride, dried over anhydrous $Na_2SO_4$, filtered and evaporated to remove all the toluene. The oily residue was used for the next reaction without further purification.

TLC: Rf=0.56 in toluene (silica gel plates), the spot turned dark-brown after spray with 5% $FeCl_3$ solution.

Preparation of 2-Benzoyloxymethylene-7-η-decyl-1-tetralone

The oily residue from the previous reaction step was mixed with dry pyridine (120 mL). The solution was stirred under nitrogen at 0° C. (ice bath). The solution was treated with 30 mL of benzoyl chloride. After the addition of the benzoyl chloride, insoluble pyridinium chloride was observed in the mixture. The reaction was stirred at room temperature for two hours. The product was poured into ice water (400 mL) with vigorous stirring. The light cream color solid was recovered by filtration and washed well with cold water. The slightly wet solid was recrystallized from hot absolute ethanol (120 mL). White solid (14 gm, 87% yield based on the 7-decyl-1-tetralone) was recovered. The melting point was 64°-66° C.

TLC: Rf=0.40 in toluene (silica gel plates)

Analysis Calculated for: $C_{28}H_{34}O_3$: C, 80.34; H, 8.19. Found: C, 80.05; H, 8.27.

Preparation of 7-η-decyl-2-methyl-1-naphthol

Cyclohexane (175 ml) was added to a mixture of 2-benzoyloxymethylene-7-(η-decyl)-1-tetralone (14 gm, 33.5 mmoles) and Pd/C (3.5 gm) under inert atmosphere. The mixture was heated to reflux while maintaining the inert atmosphere. The conversion of starting material to product was determined by thin layer chromotography after 3 hours. After all the starting material reacted, the mixture was cooled down to room temperature. The catalyst was removed by filtration and washed twice with 50 mL hot toluene. The combined filtrate was evaporated to a small volume. The product was purified with a Prep-500 silica gel column (a high pressure silica gel preparative column, obtained from Waters Association, Milford, Mass.). Toluene was used as the mobile phase. The product fractions were pooled and evaporated to dryness under vacuum overnight. Cream white solid (9.0 gm, 90% yield) was recovered: The melting point was 65°-67° C.

TLC: Rf=0.65 in toluene (silica gel plates).

Pink color developed when the product spot was irradiated with short UV light.

Analysis Calculated for: $C_{21}H_{30}O$: C, 84.51; H, 10.13. Found: C, 84.49; H, 10.72.

Preparation of 7-(η-Decyl)-2-methyl-4-(3',5'-dichlorophen-4'-one)-indonaphthol

7-Decylmethyl-1-naphthol (4.5 gm, 15.1 mmoles) and 2,6-dichloroquinone-4-chloroimide (3.0 gm, 14.3 millimoles) were dissolved in acetone (150 mL). The solution was treated with 700 mL potassium carbonate solution 0.1 M, pH=10.0). The solution was stirred vigorously at room temperature for 10 min. The pH of the reaction mixture was adjusted to 2.8 with HCl (1.0 N). The mixture was stirred for 15 minutes. The red solid was recovered by filtration and washed well with water. The solid was dissolved in toluene and filtered with glass fiber paper to remove any insoluble materials. The filtrate was concentrated and purified with Prep-500 silica gel column, using toluene as the mobile phase. Product fractions were pooled and evaporated to dryness. The residue was crystallized with η-hexane (100 mL) to give product 3.9 gm, 58% yield).

TLC: Rf=0.26 in toluene (silica gel plates).

Brown color spot, turn purple-blue after treated with 0.1 N NaOH on the plates.

Analysis Calculated for: $C_{27}H_{31}NO_2Cl_2$: C, 68.64; H, 6.57; N, 2.97. Found: C, 68.88, H, 6.85; N, 2.97.

This product, 7-decyl-MEDPIN, was used in the following experiments as the reporter substance.

11.2 Potassium Ionophore I as Ionophore

An acetone mixture was prepared containing 10.8 mg (milligrams) 7-decyl-MEDPIN and 24 mg Potassium Ionophore I. Solvent was removed under a stream of nitrogen gas. Then dried solids were combined with 4 gm of a film solution comprising 70% by weight cyclohexanone, 12% by weight vinyl chloride/vinylidene copolymer, 18% by weight diethylphthalate, and 60 μL Triton ® X-100 (a 1% by weight solution of nonionic detergent in acetone; available from Rohm and Haas, Co.). The mixture was homogenized on a vortex mixer, and then spread into a thin film on a piece of KODAR ® A150 cyclohexylene/dimethylene terephthalate copolymer (Lustro Co.) plastic, using a doctor blade having a 10 mil (0.01 inch or 254 microns) gap. The dried film has a thickness of about 3 mils (76.2 microns).

The test means was evaluated with aqueous test samples containing various potassium chloride concentrations. Each sample had 15.56 mM sodium chloride and 88.89 MM CAPS buffer [3-(cyclohexylamino)-propanesulfonic acid] and pH was adjusted to 10 with lithium hydroxide. The respective potassium chloride concentrations were 0, 0.33, 0.67 and 1.0 mM.

The evaluations were conducted by innoculating a section of the test means film with 40 microliters (μL) of test sample and the change in reflectance monitored for one minute in a SERALYZER ® reflectance Photometer (Ames Division of Miles Laboratories, Inc.).

The reflectance values (R) were converted to (K/S) in accordance with $$K/S = \frac{(1-R)^2}{2R}$$

in which R is the fraction of reflectance from the test device, K is a constant, and S is the light scattering coefficient of the particular reflecting medium. The above equation is a simplified form of the well-known Kubelka-Munk equation (See Gustav Körtum, "Reflectance Spectroscopy", pp. 106–111, Springer Verlaz, New York (1969). The data is tabulated below as (K/S) with respect to time.

| [K+] mM | (K/S) second$^{-1}$ |
|---|---|
| 0 | 0.001151 |
| 0.33 | 0.007679 |
| 0.67 | 0.01295 |
| 1.0 | 0.01909 |

As can be seen from the table, rate of change in (K/S) with time varies in accordance with potassium concentration. The data is shown graphically in FIG. I, and demonstrates easy differentiation of various potassium ion concentration levels.

11.3 Potassium Test Means Using Potassium Ionophore I and Valinomycin as Ionophores A test means film was prepared and evaluated as in Example 11.2 except that 6 mg of Potassium Ionophore I was replaced by 6 mg valinomycin. The data is reported in the following table:

| [K+] mM | (K/S) second$^{-1}$ |
|---|---|
| 0 | 0.001182 |
| 0.33 | 0.007554 |
| 0.67 | 0.01331 |
| 1.0 | 0.01857 |

The data shows a direct correlation between potassium ion concentration and rate of change of (K/S), as is clearly depicted by the graphical depiction of the data in FIG. II.

11.4 Potassium Test Means Using Equal Amounts of Potassium Ionophore and Valinomycin as Ionophores A test means film was prepared and evaluated as in Example 11.2 except that 12 mg of Potassium Ionophore was replaced by 12 mg valinomycin. The data is reported in the following table.

| [K+] mM | (K/S) second$^{-1}$ |
|---|---|
| 0 | 0.0007449 |
| 0.33 | 0.008314 |
| 0.67 | 0.01251 |
| 1.0 | 0.01898 |

The data shows a direct correlation between potassium concentration and rate of change of (K/S). This is clearly shown by the graphical plot of the data in FIG. III.

11.5 Potassium Test Means Using Valinomycin as Ionophore

A test means film was prepared and evaluated as in Example 11.2 except that the amount of 7-decyl-MEDPIN was 5.4 mg, the ratio of vinyl chloride/vinylidene chloride copolymer to diethylphthalate was adjusted to 8.55:21.45 by weight and the amount of ionophore was replaced by 12 mg valinomycin.

The aqueous test samples contained potassium chloride at concentrations of 0, 0.33, 0.67, 1.0, 2.0 and 3.0 mM. In addition, each solution contained 46.67 mM sodium chloride, 66.67 mM CAPS and was titrated to pH 10 with lithium hydroxide.

The reflectance data is reported in the following table:

| [K+] mM | (K/S) second$^{-1}$ |
|---|---|
| 0 | 0.001008 |
| 0.33 | 0.01090 |
| 0.67 | 0.01787 |
| 1.0 | 0.02872 |
| 2.0 | 0.04321 |
| 3.0 | 0.05330 |

As can be seen from the data, the test means exhibited a direct correlation between potassium ion concentration and the rate of change of (K/S) with time. As the plot of the data in FIG. IV shows, easy differentiation between potassium ion concentration levels was obtained.

11.6 Potassium Test Means Using Dipentyl Phthalate as Plasticizer

A test means film was prepared and evaluated as in Example 11.5 except that the diethylphthalate was replaced by an equal weight of dipentyl phthalate.

Aqueous test samples were as in Example 11.5 and contained potassium chloride as indicated in the table of data below:

| $[K^+]$ mM | $(K/S)$ second$^{-1}$ |
|---|---|
| 0 | 0.0005070 |
| 0.33 | 0.004041 |
| 0.67 | 0.007020 |
| 1.5 | 0.01391 |
| 3.0 | 0.02195 |

The data shows a direct correlation between potassium concentration and the rate of change of (K/S) with time. The data is plotted in FIG. V, which portrays the ease of differentiation of various potassium levels using the film test means of the present example.

11.7 Sodium Test Means

A solution of 10.8 mg 7-decyl-MEDPIN in acetone and a solution of 5 mg Sodium Ionophore I in tetrahydrofuran (THF) were mixed and the solvents removed under a stream of nitrogen. To the dried solids was added 0.5 gm of a film solution. The latter was 70% by weight cyclohexanone, 8.55% by weight of vinylchloride/vinylidene chloride copolymer, and 21.45% by weight dipentylphthalate. The mixture was homogenized on a vortex mixer and the homogenate spread into a film on a piece of KODAR ®A150 plastic using a 10 mil (254 microns) doctor blade. The dried film had a thickness of about 3 mils (76.2 microns).

Aqueous sodium test samples were prepared for evaluating the test means. Each contained 88.98 mM CAPS and potassium hydroxide was added to adjust the pH to 10. Samples were prepared containing 11.11 mM and 22.22 mM sodium chloride, respectively.

To evaluate the ability of the test means to detect sodium, 40 μL of a test sample was applied to a section of the test means film and reflectance at 640 nm was monitored over 2 minutes in a SERALYZER ® reflectance photometer. Reflectance values were converted to (K/S) values as in Example 11.2. The rate of change of (K/S) with time and respective sodium concentrations are tabulated below:

| $[Na^+]$ mM | $(K/S)$ second$^{-1}$ |
|---|---|
| 0 | 0.001459 |
| 11.11 | 0.003148 |
| 22.22 | 0.004354 |

The data shows a direct correlation between sodium ion concentration and the rate of change of (K/S) with time, as portrayed graphically in FIG. VI.

11.8 Tetrabromophenolphthalein Ethyl Ester Used as a Reporter Substance in a Test Means for Detecting Potassium A solution was prepared containing 1.8 mM valinomycin, 5 mM tetrabromophenolphthalein ethyl ester (TBEE), 5% by weight polyvinylchloride ("high molecular weight", Aldrich Chemical Co. Catalogue No. 18,956-1) and 13.1% by weight dipentyl phthalate in tetrahydrofuran. This solution was spread onto a polyester film using a 10 mil (254 microns) doctor blade, and dried.

The test means was evaluated using aqueous solutions (test samples) containing potassium chloride at concentrations of 0, 0.222, 0.556 and 1.111 mM, respectively. Each solution contained 10 mM sodium citrate (pH=5.3). The reflectance response of the test means to each test sample solution was monitored at 37° C. and 520 nm using a SERALYZER ® reflectance photometer. The results are tabulated below.

| $[K^+]$ mM | $(K/S)$ second$^{-1}$ × $10^{+2}$ |
|---|---|
| 0 | −0.0108 |
| 0.222 | 0.990 |
| 0.556 | 2.013 |
| 1.111 | 4.101 |

The data shows a direct correlation between rate of change of (K/S) per unit time and potassium concentration. FIG. VII presents this data graphically, and demonstrates a linear relationship between actual potassium ion concentration and (K/S).

11.9 Mixed Ionophores for the Determination of Potassium

It has been found that a critical ratio of 1:1 by weight, of valinomycin and Potassium Ionophore I provides a more precise test means for the determination of serum potassium. The mixed ionophore provides a test with the same reactivity but with a lower blank reaction which increases the precision of the assay. Precision is particularly important with a serum potassium assay since the concentration range of interest is both low and narrow.

A test means was prepared with a stock solution containing 12 gram PVC/PVdC, 18 gram DEP and 70 gram cyclohexanone. The film composition was as follows:

| | |
|---|---|
| Film stock solution | 1 gm |
| 7-decyl MEDPIN | 10.8 mg |
| Ionophore (total) | 24 mg |
| Triton X-100 | 60 μL (1% v:v in acetone) |

The film was drawn to a wet film thickness of 10 mil (254 microns) and dried at 70° C. for 5 to 10 minutes. To assay, aqueous potassium chloride was diluted 9-fold with 10 mM CAPS buffer, pH 10 (i.e., 1 part potassium chloride to 8 parts buffer) and applied to the film. The rate of color development at 640 nm was measured for 1 minute with an Ames SERALYZER ®.

Results of various ratios of valinomycin to Potassium Ionophore I are shown in the table below:

| Valinomycin: Potassium Ionophore I (w:w) | 0:1 | 0:1 | 1:3 | 1:3 | 1:1 | 1:1 | 1:0 |
|---|---|---|---|---|---|---|---|
| Slope of dose-response $\frac{(K/S)}{\text{sec-mM}}$ | 0.001983 | 0.001964 | 0.001910 | 0.001918 | 0.001963 | 0.001983 | 0.001911 |
| Correlation | 0.9995 | 1.000 | 0.9987 | 1.00 | 0.9946 | 1.000 | 0.9999 |
| Blank [(K/S)/sec] | 0.001151 | 0.001226 | 0.001063 | 0.001078 | 0.0007449 | 0.0007626 | 0.001101 |
| Ratio of dose slope to blank | 1.72 | 1.60 | 1.79 | 1.78 | 2.63 | 2.60 | 1.74 |

The results show that the maximum precision and minimal blank reaction occur at a 1:1 weight ratio.

11.10 Serum Potassium Correlation Study

Test means were prepared as follows. A film stock solution was prepared containing 8.55 gm PVC/PVdC, 21.45 gm diethylphthalate and 70 gm cyclohexanone. The film was prepared containing:

| Film stock solution | 1 gm |
|---|---|
| 7-decyl MEDPIN | 5.4 mg |
| Potassium Ionophore I | 6 mg |
| Triton X-100 | 0.06 mL (1% in acetone) |

The film was spread with a doctor blade to a wet film thickness of about 10 mil (254 cm) and dried at 70° C. for 5 to 10 minutes. Serum samples were diluted threefold (1 part serum to 2 parts CAPS buffer pH 10, 100 mM) and applied to the film. The rate of color development at 640 nm was measured for 1 minute with an Ames SERALYZER ® reflectance photometer. FIG. VIII shows the correlation of the reactivity of the potassium film to the potassium ion concentration in millimoles per liter before 3 fold dilution as determined by flame emission spectrophotometry. The regression coefficient of the correlation line is 0.9817 indicating very good correlation of the test means results with serum potassium in the concentration range (3 mM to about 7.5 mM) of clinical interest.

Obviously many other modifications and variations can be made without departing from the spirit and scope of the invention.

What is claimed is:

1. A test means for determining the presence of an ion in an aqueous test sample, the test means comprising: a reagent layer composed of a substantially nonpolar, nonporous carrier matrix incorporated with
    (a) an ionophore capable of forming a complex with a specific ion to be determined, and
    (b) a reporter substance capable of interacting with the complex of the ionophore and the ion to produce a detectable response.
2. The test means of claim 1 in which the nonpolar, nonporous carrier matrix is a polymer film.
3. The test means of claim 2 in which the polymer film includes a plasticizer.
4. The test means of claim 3 in which the reporter substance is formed by at least two precursor substances incorporated in the nonpolar, nonporous carrier matrix, which formation is caused by the interaction of the precursor substances with the complex of the ionophore and the ion.
5. The test means of claim 3 in which the polymer film is additionally incorporated with light scattering centers.
6. The test means of claim 5 in which the light scattering centers are composed of particles selected from the group consisting of titanium dioxide, aluminum oxide, magnesium oxide, calcium carbonate, barium sulfate, zinc oxide, lead oxide, talc and microcrystalline cellulose.
7. A test means for determining the presence of an ion in an aqueous test sample, the test means comprising a reagent layer composed of a substantially nonpolar, nonporous carrier matrix incorporated with
    (a) an ionophore capable of forming a complex with a specific ion to be determined; and
    (b) a neutral reporter compound having a dissociable proton, which proton is capable of dissociating from the reporter upon interaction with the complex of the ionophore and the ion to produce a detectable response.
8. The test means of claim 7, which additionally includes a water impervious support member affixed to the reagent layer.
9. The test means of claim 7 in which the nonpolar, nonporous carrier is a polymer film.
10. The test means of claim 9 in which the polymer film includes a plasticizer.
11. The test means of claim 7 in which the reporter substance is one capable of producing the appearance of, or change in, fluorescence in the presence of the complex of the ionophore and the ion.
12. The test means of claim 11 in which the reporter substance is fluorescein or a derivative thereof.
13. The test means of claim 7 in which the reporter substance is one capable of producing the appearance of, or change in, color in the presence of the complex of the ionophore and the ion.
14. The test means of claim 13 in which the reporter substance is a compound having the structure:

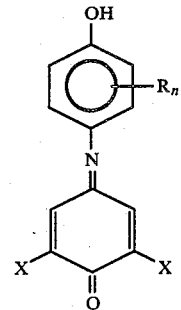

in which X, same or different, is a halogen or pseudohalogen; in which each R, same or different, is a 2-, 3-, 5-, or 6-position substitutent, or multiple substituents thereof, selected from the lower alkyl, intermediate alkyl, aryl or fused ring at the 2,3- or 5,6-position; and $\eta$ is 0 to 4.

15. The test means df claim 13 in which the reporter substance is a compound having the structure:

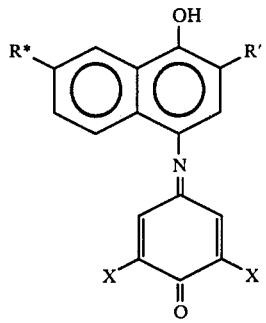

in which R' is H or lower alkyl, R* is H or intermediate alkyl and X, same or different, is halogen or pseudohalogen.

16. The test means of claim 15 in which R' is methyl and R* is $\eta$-decyl.

17. The test means of claim 16 in which the specific cation to be determined is potassium ion and the ionophore is composed of valinomycin and 2,3-naphtho-1,4,7,10,13-pentaoxacyclopentadeca-2-ene.

18. A multilayer test means for determining the presence of an ion in an aqueous test sample, comprising:
(a) a reagent layer comprising a substantially nonpolar, nonporous carrier matrix incorporated with an ionophore capable of forming a complex with a specific ion to be determined and a reporter substance capable of interacting with the complex of the ionophore and the ion to produce a detectable response, and
(b) a reflecting layer disposed on top of the reagent layer and in laminar relationship thereto, said reflecting layer including one or more materials which act as a background in order to facilitate the detection of a detectable response in the reagent layer.

19. The process of determining unbound calcium, comprising the steps of:
(a) contacting the reflecting layer of the multilayer test means of claim 18 with an aqueous test sample; and
(b) determining the detectable response in the reagent layer.

20. The multilayer test means of claim 18 in which the specific ion to be determined is a cation and the reporter is a neutral compound having a dissociable proton, which proton is capable of dissociating from the reporter upon interaction of the reporter with the complex of the ionophore and the ion to produce a detectable response.

21. The multilayer test device of claim 18 which additionally includes a buffer incorporated with the reflecting layer.

22. The multilayer test device of claim 18 which additionally includes an interferant removal substance incorporated with the reflecting layer.

23. The multilayer test means of claim 18 in which the background material in the reflecting layer is composed of particles selected from the group consisting of titanium dioxide, aluminum oxide, magnesium oxide, barium sulfate, zinc oxide, lead oxide, talc and microcrystalline cellulose.

24. The multilayer test means of claim 23 in which the reflecting layer additionally includes a hydrophilic polymer.

25. The multilayer test means of claim 18 in which the nonpolar, nonporous carrier matrix is a polymer film.

26. The multilayer test means of claim 25 in which the polymer film includes a plasticizer.

27. The multilayer test means of claim 26 additionally comprising a transparent support member laminated to the reagent layer on the side opposed to the reflecting layer.

28. The multilayer test means of claim 18 additionally comprising an opacifying layer in laminar relationship to the reflecting layer and disposed on top of the reflecting layer, the opacifying layer containing particles for imparting an opaque appearance to the opacifying layer.

29. The multilayer test means of claim 28 in which the opacifying particles are particles of carbon black.

30. The multilayer test means of claim 28 in which the opacifying layer additionally includes a hydrophilic polymer.

31. The multilayer test device of claim 28 which additionally includes a buffer incorporated with the reflecting layer, the opacifying layer or both.

32. The multilayer test device of claim 28 which additionally includes an interferant removal substance incorporated with the reflecting layer, the opacifying layer or both.

33. A multilayer test means for determining the presence of an ion in a whole blood sample, comprising:
(a) a reagent layer comprising a substantially nonpolar, nonporous carrier matrix incorporated with an ionophore capable of forming a complex with a specific ion to be determined and reporter substance capable of interacting with the complex of the ionophore and the ion to produce a detectable response, and
(b) a reflecting layer disposed on top of the reagent layer and in laminar relationship thereto, said reflecting layer including one or more materials wlich act as a background in order to facilitate the detection of a response in the reagent layer and sufficient sodium chloride to impart hematocrit independence to the ion determination.

34. A multilayer test means for determining the presence of an ion in a whole blood sample, comprising:
(a) a reagent layer comprising a substantially nonpolar, nonporous carrier matrix incorporated with an ionophore capable of forming a complex with a specific ion to be determined and a reporter substance capable of interacting with the complex of the ionophore and the ion to produce a detactable response;
(b) a reflecting layer disposed on top of the reagent layer and in laminar relationship thereto, said reflecting layer including one or more materials which act as a background in order to facilitate the detection of a response in the reagent layer; and
(c) an opacifying layer in laminar relationship to the reflecting layer and disposed on top of the reflecting layer, the opacifying layer containing particles for imparting an opaque appearance to the opacifying layer;
wherein sufficient sodium chloride is incorporated in either the reflecting layer, the opacifying layer or both, to impart hematocrit independence to the ion determination.

* * * * *